United States Patent [19]
Tachikawa

[11] Patent Number: 6,054,602
[45] Date of Patent: Apr. 25, 2000

[54] METHOD OF MAKING AN AROMATIC CHLOROSILANE COMPOUND BY A HYDROSILATION REACTION

[75] Inventor: Mamoru Tachikawa, Kanagawa, Japan

[73] Assignee: Dow Corning Asia, Ltd., Tokyo, Japan

[21] Appl. No.: 09/342,800

[22] Filed: Jun. 29, 1999

[30] Foreign Application Priority Data

Jun. 29, 1998 [JP] Japan .................. 10-182009

[51] Int. Cl.$^7$ ....................................... C07F 7/08
[52] U.S. Cl. ............................................. 556/479
[58] Field of Search .............................. 556/479

[56] References Cited

U.S. PATENT DOCUMENTS

| | | | |
|---|---|---|---|
| 5,424,470 | 6/1995 | Bank et al. | 556/479 |
| 5,481,016 | 1/1996 | Bank et al. | 556/479 |
| 5,486,637 | 1/1996 | Bank et al. | 556/479 |
| 5,616,763 | 4/1997 | Bank et al. | 556/479 |
| 5,623,083 | 4/1997 | Bank et al. | 556/479 |
| 5,756,795 | 5/1998 | Bank et al. | 556/479 |

*Primary Examiner*—Paul F. Shaver
*Attorney, Agent, or Firm*—William F. Boley

[57] ABSTRACT

A process comprising the hydrosilation of an aromatic vinyl compound by a hydridochlorosilane compound in the present of platinum or platinum compound and a carboxylic acid. The process favors the formation of the β-adduct of the hydrosilation reaction.

10 Claims, No Drawings

METHOD OF MAKING AN AROMATIC CHLOROSILANE COMPOUND BY A HYDROSILATION REACTION

BACKGROUND OF INVENTION

The present invention is a method of making aromatic chlorosilane compounds, having important industrial application as silane coupling agents and for modifying silicones, by hydrosilating an aromatic vinyl compound with a hydridochlorosilane compound in the presence of a platinum or platinum compound catalyst and a carboxylic acid compound, which imparts a high positional selectivity to the hydrosilation reaction.

Functional chlorosilanes are silicon-containing compounds which find important industrial applications as raw materials for modifying silicones and as silane coupling agents. In order to impart to silane coupling agents and modified silicones an improved resistance to heat, to control their refraction indices, and to improve their compatibility with organic compounds and polymers, aromatic substituents are often introduced into their structures. The following are examples of compounds that contain aromatic groups: phenyl silicon compounds in which silicon is bonded directly to an aromatic ring, e.g., phenylsilane compounds and phenylsilicone derivatives; compounds in which aromatic groups are bonded to silicon via hydrocarbon groups, e.g., a benzylsilane compound; and silicone derivatives having 3-phenylpropyl groups or phenethyl groups, or similar aralkyl-type silicon compounds.

Among the above, phenyl groups which are bonded directly to silicon are formed as a result of a reaction between silicon metal and chlorobenzene (so-called "direct process"), a reaction of removal of hydrogen from benzene and hydridochlorosilane in the presence of a boron chloride catalyst, or an equivalent organic reaction such as a Grignard method. Aralkyl silicon bonds can also be produced by an equivalent organic reaction such as a Grignard method. However in the case of 3-phenylpropyl groups or phenethyl groups, it would be more economical to utilize a reaction of hydrosilation of aromatic compounds such as styrene or a similar compound having unsaturated groups. In particular, many vinyl substituents of styrene, naphthalene, pyridine, or similar aromatic compounds, as well as many vinyl substituents of derivatives of styrene, naphthalene, and pyridine are known, commercially available, and suitable for synthesis of silicon compounds having aromatic substituents.

It is known that hydrosilation of aromatic compounds having a vinyl substitution is normally accompanied by the formation of both α- and β-adducts to the aromatic ring. In particular, when a hydridochlorosilane is used as the silane the β-adducts are more readily hydrolyzed than the α-adducts and therefore the formation of β-adducts is typically more desirable. Another reason it is preferable to use methods for synthesis of β-adducts alone is that it is not easy to separate α- and β-adducts from a mixture.

It has been reported that the above problem can be solved by modifying a platinum catalyst with a ligand of a phosphorus compound such as an organic phosphine. However, since the use of such a phosphorus-modified platinum catalyst noticeably reduces activity, the reaction requires a long time and high temperature. Therefore, this method of solving the above mentioned problem is not entirely satisfactory since vinyl groups which are bonded directly to aromatic groups normally have high polymerization activity, and, if the hydrosilation reaction is carried out for a sufficiently long time and at high temperature polymerization of vinyl groups occurs whereby the vinyl compound is lost.

It is an object of the present invention to increase the amount of β-adducts to aromatic rings in a method of making an aromatic chlorosilane compound by hydrosilation of an aromatic compound having a vinyl group directly bonded to the aromatic ring (hereinafter referred to as "aromatic vinyl compound") with a hydridochlorosilane compound. It is another object to provide a method of making an aromatic trichlorosilane compound comprising the β-adduct essentially without making the α-adduct.

SUMMARY OF INVENTION

The present invention is a method of making an aromatic chlorosilane compound comprising the hydrosilation of an aromatic vinyl compound by a hydridochlorosilane compound in the present of platinum or platinum compound and a carboxylic acid. The process favors the formation of the β-adduct of the hydrosilation reaction.

DESCRIPTION OF INVENTION

The present invention comprises a method of making aromatic chlorosilane compounds by hydrosilating an aromatic vinyl compound with a hydridochlorosilane in the presence of platinum or a platinum compound catalyst and a carboxylic acid compound. Among the aromatic chlorosilane compounds obtained by the present method, the desired compound has a β-adduct in an aromatic ring with one or two silicon atoms bonded to an aromatic group via an ethylene group, the silicon atom(s) being directly bonded to 1 to 3 chlorine atoms.

The aromatic vinyl compound of the present invention is an aromatic compound in which a vinyl group is bonded directly to the aromatic ring. There are no special limitations, provided this condition is satisfied. For example the aromatic vinyl compound can be a monocyclic aromatic vinyl compound, a polycyclic aromatic vinyl compound, a nonbenzonoid aromatic vinyl compound, a vinyl metallocene compound, or derivatives of the aforementioned compounds. The following are specific examples of such aromatic vinyl compounds: styrene, vinylnaphthalene, vinylfuran, vinylthiofuran, vinylpyrrole, vinylpyridine, vinylmetallocene compound, or derivatives of the aforementioned compounds. Examples of such derivatives are aromatic compounds which have in their structure at least one atom of an element selected from the group consisting of oxygen, nitrogen, fluorine, chlorine, bromine, iodine, sulfur, or silicon. Examples of preferred aromatic vinyl compounds are styrene, vinylnaphthalene, vinylfuran, or their derivatives.

The following are specific examples of the aromatic vinyl compound: styrene, paraphenylstyrene, parachlorostyrene, paramethylstyrene, paramethoxystyrene, paratrimethylsilylstyrene, methachlorostyrene, parabromostyrene, chloromethylstyrene, divinylbenzene, vinylnaphthalene, vinylantracene, vinylfuran, vinylthiophene, vinylpyrol, vinylpyridine, vinylferrocene, and vinylcyclopentadienyl mangantricarbonyl.

A hydridochlorosilane compound suitable for the purposes of the present invention is represented by formula (1) given below and is a silicon compound having at least one chlorine atom bonded to the silicon atom and one or two hydrogen atoms bonded directly to the silicon atom.

$$H_n SiR_m Cl_{(4-n-m)} \quad (1)$$

where n is 1 or 2, m is 0, 1, or 2; 4-n-m≧1, and R is an organic group having 1 to 10 carbon atoms.

The substituent, R, is an organic group having 1 to 10 carbon atoms. Preferably, R is a hydrocarbon group having at least one atom selected from the group consisting of oxygen, fluorine, chlorine, bromine, iodine, and silicon atom. The following are examples of aforementioned organic groups: hydrocarbon groups, such as an alkyl group, e.g., methyl, ethyl, n-propyl, isopropyl, n-butyl, t-butyl, pentyl, hexyl, octyl, and decyl; an alkenyl group, e.g., 2-propenyl, hexenyl, and octenyl; an aralkyl group, e.g., benzyl and phenethyl; an aryl group, e.g., phenyl, tolyl, and xylyl; as well as hydrocarbon substituents having 1 to 10 carbon atoms and containing at least one atom selected from the group consisting of oxygen, halogen, and silicon atoms, for example, chloromethyl, 4-chlorophenyl, trimethylsilylmethyl, 2-methoxyethyl, and 3,3,3-trifluoropropyl.

A specific example of the hydridochlorosilane compound having one hydrogen atom bonded to a silicon atom is a trichlorosilane; examples of hydridochlorosilane compounds having two chlorine atoms bonded to the silicon atom are the following: methyldichlorosilane, ethyldichlorosilane, n-propyldichlorosilane, isopropyldichlorosilane, n-hexyldichlorosilane, n-octyldichlorosilane, phenyldichlorosilane, (trifluoropropyl)dichlorosilane, (chloromethyl)dichlorosilane, (trimethylsilylmethyl)dichlorosilane, benzyldichlorosilane, and vinyldichlorosilane. Examples of hydridochlorosilane compounds having one chlorine atom are the following: dimethylchlorosilane, diethylchlorosilane, n-propylmethylchlorosilane, isopropylmethylchlorosilane, n-hexylmethylchlorosilane, n-octylmethylchlorosilane, diphenylchlorosilane, (trifluoropropyl)methylchlorosilane, (chloromethyl)methylchlorosilane, (trimethylsilylmethyl)methylchlorosilane, benzylmethylchlorosilane, and vinylmethylchlorosilane.

An example of a hydridochlorosilane compound having two hydrogen atoms bonded to a silicon atom is dichlorosilane. The following are examples of hydridochlorosilane compounds having one chlorine atom bonded to a silicon atom: methylchlorosilane, ethylchlorosilane, n-propylchlorosilane, isopropylchlorosilane, n-hexylchlorosilane, n-octylchlorosilane, phenylchlorosilane, (trifluoropropyl)chlorosilane, (chloromethyl)chlorosilane, (trimethylsilylmethyl) chlorosilane, benzylchlorosilane, and vinylchlorosilane. Most preferred for the present method are hydridochlorosilane compounds having in the aforementioned formula (1) a value of n equal to 1. Examples of these compounds are trichlorosilane, alkyldichlorosilane, and dialkylchlorosilane.

A carboxylic acid compound suitable for the purposes of the present method can be any compound listed in items a through f below:

a) carboxylic acid (without any special limitations, provided there is a carboxyl group; the following are examples of the carboxylic acids: saturated carboxylic acid, unsaturated carboxylic acid, monocarboxylic acid, and dicarboxylic acid. In the carboxylic acids, portions other than the carboxylic groups are normally selected from saturated or unsaturated aliphatic hydrocarbon groups, aromatic hydrocarbon groups, halogenated hydrocarbon groups, or hydrogen atoms. The aforementioned hydrocarbon groups may be bonded to amine groups, silyl groups, hydroxyl groups, or similar substituents.)

b) carboxylic acid anhydride, c) silyl compound of carboxylic acid, d) alkali metal salt of carboxylic acid, e) alkali earth metal salt of carboxylic acid, and f) a carboxylic acid compound of the type a) to e) produced as a result of decomposition or reaction which occurs in the present method during the hydrosilation reaction.

In the present method the carboxylic acid compound can be added either prior to the hydrosilation reaction or at the initial stage of the hydrosilation reaction. The carboxylic acid compound can be, for example, the aforementioned carboxylic acid, silyl compound of carboxylic acid, carboxylic acid anhydride, alkali metal salt of carboxylic acid, and alkali earth metal salt of carboxylic acid. However, in addition to compounds mentioned above, the method may also contain compounds which form the aforementioned carboxylic acid compounds as a result of decomposition or reaction. The following are specific examples of the aforementioned compounds: carboxylic acids such as saturated monocarboxylic acids such as formic acid, acetic acid, propionic acid, n-butyric acid, isobutyric acid, hexanoic acid, cyclohexanoic acid, lauric acid, and stearic acid; saturated dicarboxylic acids such as oxalic acid and adipic acid, aromatic carboxylic acids such as benzoic acid and para-phthalic acid; a silated carboxylic acid such as trimethylsilyl acetic acid, para-chlorobenzoic acid, trifluoroacetic acid, dichloroacetic acid, and chloroacetic acid in which the hydrogen atom in the hydrocarbon group of the carboxylic acid is substituted by a halogen atom or an organosilyl group; an unsaturated aliphatic acid such as an acrylic acid, methacrylic acid, and oleic acid. The carboxylic acid also can be a compound which in addition to the carboxylic group may contain a hydroxy group, carbonyl group, or an amino group, for example a hydroxy acid such as a lactic acid; a keto acid such as acetoacetic acid; an aldehydic acid such as glyoxylic acid; and an amino acid such as glutamic acid.

The following are examples of silyl compounds of the carboxylic acid: trialkylsilylcarboxylates such as timethylsilyl formate, trimethylsilyl acetate, triethylsilyl propionate, trimethylsilyl benzoate, trimethylsilyltrifluoroacetate; di-, tri-, or tetra-carboxysilanes such as dimethyldiacetoxysilane, diphenyldiacetoxysilane, methyltriacetoxysilane, vinyltriacetoxysilane, and silicon-tetrabenzoate.

The carboxylic acid anhydrides can be, for example, anhydrous acetic acid, anhydrous propionic acid, and anhydrous benzoic acid. Alkali metal salts and alkali earth metal salts can be, for example, sodium formate, lithium formate, potassium formate, sodium acetate, lithium acetate, calcium acetate, potassium acetate, sodium benzoate, lithium benzoate, cesium benzoate, lithium laurate, and sodium stearate.

Compounds formed as a result of decomposition or a reaction with the carboxylic acid compounds can comprise carboxylic acid halides, such as acetyl chloride, butyryl chloride, and benzoyl chloride; optically or thermally decomposable carboxylic acid esters such as acetic acid (2-nitrobenzyl); and carboxylic acid esters such as a methyl acetate which form the aforementioned carboxylic acid compounds as a result of a reaction with a silicon-bonded halogen; or carboxylic acid salts such as thallium acetate which form carboxylic acid compounds as a result of a reaction with halogen bonded to the silicon atom.

The carboxylic acid compounds are added to the reaction system in an amount of 0.001 weight percent to 20 weight percent. However, it is preferred that they are added in an amount from 0.01 weight percent to 10 weight percent.

The term the "reaction system" in the context of the present invention is a mixture of the hydridochlorosilane compound, an aromatic vinyl compound, a platinum catalyst, and the carboxylic acid compound.

There are no specific limitations with regard to the catalyst, provided that the hydrosilation catalyst is platinum or a platinum compound which is normally used for the purpose of hydrosilation. Such a catalyst can be selected from a particulate carrier bound platinum, platinum colloid; a negatively-charged complex or zero-valence, bivalent, or tetra-valent platinum compound. More specifically, the particulate carrier bound platinum can be represented by activated carbon-carrier bonded platinum, alumina-carrier bonded platinum, silica-carrier bonded platinum. Examples of negatively-charged complexes of platinum are platinum carbonyl anionic compounds (J. Amer. Chem. Soc., 1976, 98, 7225) such as $[Pt_3(CO)_6]^{2-}$, $[Pt_3(CO)_6]^{22-}$, $[Pt_3(CO)_6]^{42-}$. Examples of zero-valance platinum compounds are Pt(0)-divinyltetramethyldisiloxane complex, Pt (0)-tetravinyltetramethylcyclotetrasiloxane complex, Pt(0)-ethylene complex, and Pt(0)-styrene complex. The bivalent platinum compounds are exemplified by $Pt(II)Cl_2$, $Pt(II)Br_2$, bis-(ethylene) $Pt(II)Cl_2$, (1,5-cyclooctadiene) $Pt(II)Cl_2$, Pt(II) acetylacetonate, and bis-(benzonitrile) $Pt(II)Cl_2$. Examples of tetra-valent platinum compounds are $Pt(IV)Cl_4$, $H_2Pt(IV)Cl_6$, $Na_2Pt(IV)Cl_6$, $K_2Pt(IV)Cl_6$.

The most preferred platinum and platinum compound catalyst from the point of view of solubility in organic solvent and stability of the catalytic solution is an alcoholic solution of chloroplatinic acid and Pt(0)-divinyltetramethyldisiloxane complex. The amount of catalyst required in the present method will depend on such conditions as the reactants, reaction temperature, and reaction time. Therefore, no single recommendation exists with regard to the selection of the quantity of the catalyst required. In general, however, platinum should be used in an amount of $10^{-3}$ moles to $10^{-8}$ moles per 1 mole of the aromatic vinyl compound, whereas from the point of view of cost of the catalyst and from the standpoint of reaction time, a range of $10^{-4}$ to $10^{-7}$ moles platinum per mole of the aromatic vinyl compound would be more suitable.

The reaction temperature may vary from 0° C. to 300° C., but, to achieve an optimum reaction rate and from the point of view of better stability of the product and the aromatic vinyl compound, the reaction temperature range is preferably between 30° C. to 250° C.

A solvent is not required for the present method. However, for the purposes of dissolving the aromatic vinyl compound, in order to facilitate addition of the catalytic component, and to control the reaction system temperature a reaction solvent for the hydrocarbon-type compounds and a solvent for the catalytic components can be used. The following are examples of suitable solvents for the above purposes: saturated or unsaturated hydrocarbons such as hexane, cyclohexane, heptane, octane, dodecane, benzene, toluene, xylene, dodecylbenzene; halogenated hydrocarbons such as chloroform, methyl chloride, chlorobenzene, orthodichlorobenzene; oxygen-contained organic compounds such as ether, tetrahydrofuran; and silicone compounds such as hexamethyldisiloxane, and polydimethylsiloxane.

The reaction may be carried out in air, in nitrogen, in argon, or in a similar inert gas environment. It is preferred that the reaction be conducted under a low partial pressure of oxygen or without the presence of oxygen.

The following examples are provided to illustrate the present invention and are not intended to limit the claims herein.

Practical Example 1

Reaction between styrene and trichlorosilane in the presence of a platinum catalyst and acetic acid. A tube was filled with 416 mg of styrene, 540 mg of trichlorosilane, and 208 mg of toluene. Then 0.005 ml of acetic acid was added to the tube by means of a microsyringe. The tube content was then combined with 0.005 ml of a toluene solution of a zero-valence platinum complex of divinyltetramethyldisiloxane (platinum quantity 0.04 Wt. %). The tube was sealed with Teflon tape and immersed in an oil bath for 1.5 hours at 50° C. After cooling, the tube content was analyzed by gas chromatography which showed that the degree of conversion of styrene was 9.5%. The yield of phenethyltrichlorosilane was 7.3%. Formation of (1-phenylethyl) trichlorosilane was not observed.

Comparative Example 1

Reaction between styrene and trichlorosilane in the presence of a platinum catalyst without the addition of a carboxylic acid compound. A tube was filled with 416 mg of styrene, 540 mg of trichlorosilane, and 208 mg of toluene. Then 0.005 ml of a toluene solution of a zero-valence platinum complex of divinyltetramethyldisiloxane (platinum quantity 0.04 Wt. %) was added. The tube was sealed with Teflon tape and immersed in an oil bath for 1.5 hours at 50° C. After cooling, the tube content was analyzed by gas chromatography which showed that the degree of conversion of styrene was 21%. The total yield of phenethyltrichlorosilane and (1-phenylethyl)trichlorosilane was 16.7%. Selectivity for the β-silyl compound (phenethyl form) was 98.7%.

Practical Example 2

Reaction between styrene and methyldichlorosilane in the presence of a platinum catalyst and acetic acid. A tube was filled with 416 mg of styrene, 460 mg of methyldichlorosilane, and 208 mg of toluene. Then, 0.005 ml of acetic acid was added to the tube by means of a microsyringe. The tube content was then combined with 0.001 ml of a toluene solution of a zero-valence platinum complex of divinyltetramethyldisiloxane (platinum quantity 0.4 Wt. %). The tube was sealed with Teflon tape and immersed in an oil bath for 30 minutes at 50° C. After cooling, the tube content was analyzed by gas chromatography which showed that the degree of conversion of styrene was 11%. The total yield of phenethylmethyldichlorosilane and (1-phenylethyl)methyldichlorosilane was 10.3%. Selectivity for the β-silyl compound (phenethyl form) was 98.4%.

Comparative Example 2

Reaction between styrene and methyldichlorosilane in the presence of a platinum catalyst without the addition of a carboxylic acid compound The reaction was carried out in a manner similar to that of Practical Example 2 except that acetic acid was not added. The degree of conversion of styrene was 29%. The yield of phenethyldichlorosilane was 14.7% and the yield of (1-phenylethyl) methyldichlorosilane was 12.1%.

Practical Example 3

Reaction between styrene and dimethylchlorosilane in the presence of a platinum catalyst and acetic acid. A tube was filled with 416 mg of styrene, 378 mg of dimethylchlorosilane, and 208 mg of toluene. Then, 0.005 ml of acetic acid was added by means of a microsyringe. The tube content was then combined with 0.001 ml of a toluene solution of a zero-valence platinum complex of divinyltetramethyldisiloxane (platinum quantity 0.4 Wt. %). The tube was sealed with Teflon tape and immersed in an oil bath at 50° C. overnight. After cooling, the tube content was analyzed by gas chromatography which showed that the degree of conversion of styrene was 86%. The total yield of phenethyldimethylchlorosilane and (1-phenethyl) dimethyichlorosilane was 83%. Selectivity for the β-silyl compound (phenethyl form) was 98.0%.

Comparative Example 3

Reaction between styrene and dimethylchlorosilane in the presence of a platinum catalyst without addition of a carboxylic acid compound. A tube was filled with 416 mg of styrene, 378 mg of dimethylchlorosilane, and 208 mg of toluene. Then, 0.001 ml of a toluene solution of a zero-valence platinum complex of divinyltetramethyldisiloxane (platinum quantity 0.4 Wt. %) was added. The tube was sealed with Teflon tape and immersed in an oil bath at 50° C. for half an hour. After cooling, the tube content was subjected to gas chromatography analysis which showed that the degree of conversion of styrene was 76%. The total yield of phenethyldimethylchlorosilane and (1-phenethyl) dimethylchlorosilane was 71.2%. Selectivity for the β-silyl compound (phenethyl form) was 80.8%.

Comparative Example 5

Reaction between vinylbenzyl chloride and dimethylchlorosilane in the presence of a platinum catalyst without addition of a carboxylic acid compound. A tube was filled with 373 mg of vinylbenzyl chloride (a mixture of para- and meta-forms), 288 mg of dimethylchlorosilane, and 90 mg of toluene. Then, 0.001 ml of a toluene solution of a zero-valence platinum complex of divinyltetramethyldisiloxane (platinum quantity 0.4 Wt. %) was added. The tube was sealed with Teflon tape and immersed in a 55° C. oil bath for 14 hours. After cooling, the tube content was analyzed by gas chromatography which showed that the degree of conversion of vinylbenzyl chloride was 77%. The total yield of {1-(chloromethylphenyl) ethyl}dimethylchlorosilane and {2-(chloromethylphenyl) ethyl}dimethylchlorosilane was 58%. Selectivity for the β-silyl compound (2-(chloromethylphenyl) ethyl form) was 81%.

Practical Example 4

Reaction between divinylbenzene and dimethylchlorosilane in the presence of a platinum catalyst and ethyltriacetoxysilane. A tube was filled with 170 mg of divinylbenzene (purity 80%, the balance being ethylstyrene), 309 mg of dimethylchlorosilane, and 40 mg of toluene. Then, 0.02 ml of ethyltriacetoxysilane was added to the tube. The tube content was then combined with 0.01 ml of a toluene solution of a zero-valence platinum complex of divinyltetramethyldisiloxane (platinum quantity 0.4 Wt. %). The tube was sealed with Teflon tape and immersed in a 55° C. oil bath for 15 hours. After cooling, the tube content was analyzed by gas chromatography which showed that the divinylbenzene was completely consumed. The yield of {1-(ethylphenyl)ethyl} dimethylchlorosilane and {2-(ethylphenyl)ethyl} dimethylchlorosilane was 0.3% and 15%, respectively. The yield of bis-(dimethychlorosilylethyl) benzene was 73%. Selectivity for the β-(silyl compound of bis-(dimethychlorosilylethyl) benzene was 98.7%.

Comparative Example 6

Reaction between divinylbenzene and dimethylchlorosilane in the presence of a platinum catalyst without addition of a carboxylic acid compound. A tube was filled with 170 mg of divinylbenzene (purity 80%, the balance being ethylstyrene), 309 mg of dimethylchlorosilane, and 40 mg of toluene. Then 0.01 ml of a toluene solution of a zero-valence platinum complex of divinyltetramethyldisiloxane (the platinum quantity 0.4 Wt. %) was added. The tube was sealed with Teflon tape and immersed in a 55° C. oil bath for 15 hours. After cooling, the tube content was analyzed by gas chromatography which showed that the divinylbenzene was consumed completely. The yield of {1-(ethylphenyl)ethyl}dimethylchlorosilane and {2-(ethylphenyl) ethyl}dimethylchlorosilane was 5% and 10%, respectively. The yield of bis-(dimethychlorosilylethyl) benzene was 79%. Selectivity for the β-(silyl compound of bis-(dimethychlorosilylethyl) benzene) was 76%.

I claim:

1. A method of making an aromatic chlorosilane compound comprising hydrosilating an aromatic vinyl compound with a hydridochlorosilane compound in the presence of a platinum or a platinum compound catalyst and a carboxylic acid compound, with the proviso that the carboxylic acid compound is not maleic anhydride.

2. The method of claim 1, where the aromatic vinyl compound is selected from the group consisting of styrene, vinylnaphthalene, vinylfurane, and their derivatives, the hydridochlorosilane compound is described by formula $$H_nSiR_mCl_{(4-n-m)}$$

where n is 1 or 2, m is 0, 1 or 2, 4-n-m≧1 and R represents an organic groups having 1 to 10 carbon atoms.

3. The method of claim 1 where the carboxylic acid compound is selected from the group consisting of carboxylic acid, silylated carboxylic acid compound, carboxylic acid anhydride with the proviso that the carboxylic acid anhydride is not maleic anhydride, alkali metal salt of a carboxylic acid, and alkaline-earth metal salt of a carboxylic acid, the carboxylic acid compound being present in an amount from 0.01 weight percent to 20 weight percent.

4. The method of claim 2 where the carboxylic acid compound is selected from the group consisting of carboxylic acid, silylated carboxylic acid compound, carboxylic acid anhydride with the proviso that the carboxylic acid anhydride is not maleic anhydride, alkali metal salt of a carboxylic acid, and alkaline-earth metal salt of a carboxylic acid, the carboxylic acid compound being present in an amount from 0.01 weight percent to 20 weight percent.

5. The method of claim 1 where the hydridochlorosilane compound is described by formula $$H_nSiR_mCl_{(4-n-m)}$$

where n is 1 or 2, m is 0, 1 or 2, 4-n-m≧1 and R represents an organic group having 1 to 10 carbon atoms and the carboxylic acid compound is selected from the group consisting of carboxylic acid, silylated carboxylic acid compound, carboxylic acid anhydride with the proviso that the carboxylic acid anhydride is not maleic anhydride, alkali metal salt of a carboxylic acid, and alkaline-earth metal salt of a carboxylic acid.

6. The method of claim 5 where the aromatic vinyl compound is selected from the group consisting of styrene, vinylnaphthalene, vinylfurane, and their derivatives.

7. The method of claim 5 where the catalyst is selected from the group consisting of an alcoholic solution of chloroplatinic acid and Pt(0)-divinyltetramethylsiloxane complex.

8. The method of claim 6 where the catalyst is selected from the group consisting of an alcoholic solution of chloroplatinic acid and Pt(0)-divinyltetramethylsiloxane complex.

9. The method of claim 5 where the carboxylic acid is present in an amount from 0.01 weight percent to 10 weight percent.

10. The method of claim 8 where the carboxylic acid is present in an amount from 0.01 weight percent to 10 weight percent.

* * * * *